United States Patent [19]

Gainer

[11] Patent Number: 5,102,932
[45] Date of Patent: Apr. 7, 1992

[54] FLAME RETARDANTS FOR POLYMERS

[75] Inventor: James Gainer, Boothstown, England

[73] Assignee: Ciba-Geigy Corporation, Ardsley, N.Y.

[21] Appl. No.: 675,214

[22] Filed: Mar. 26, 1991

[30] Foreign Application Priority Data

Apr. 3, 1990 [GB] United Kingdom ............. 9007515

[51] Int. Cl.$^5$ ............. C07F 9/38; C07F 9/40; C08K 5/5333
[52] U.S. Cl. ................... 524/130; 556/174
[58] Field of Search ............. 524/130, 123; 556/174

[56] References Cited

U.S. PATENT DOCUMENTS

| | | | |
|---|---|---|---|
| 3,576,923 | 4/1971 | Randell et al. | 558/211 |
| 4,939,285 | 7/1990 | Weis et al. | 556/19 |
| 4,972,011 | 11/1990 | Richardson et al. | 524/130 |
| 4,973,727 | 11/1990 | Gainer et al. | 556/19 |

FOREIGN PATENT DOCUMENTS

| | | |
|---|---|---|
| 245207 | 11/1987 | European Pat. Off. |
| 321002 | 6/1989 | European Pat. Off. |
| 327496 | 8/1989 | European Pat. Off. |
| 2211850 | 7/1989 | United Kingdom |

*Primary Examiner*—Veronica P. Hoke
*Attorney, Agent, or Firm*—Luther A. R. Hall

[57] ABSTRACT

A reaction of alumina trihydrate, dimethyl methylphosphonate and a phosphonic acid of formula

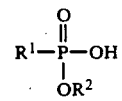

where $R^1$ denotes an alkyl group of 1 to 4 carbon atoms, optionally substituted by at least one group selected from a hydroxyl group, a carboxyl group or a phosphonic acid group $—P(O)(OH)_2$, or a $C_6$ to $C_{12}$ aryl group and $R^2$ denotes a hydrogen atom or an alkyl group of 1 to 4 carbon atoms, is useful as a flame retardant for polymers.

20 Claims, No Drawings

FLAME RETARDANTS FOR POLYMERS

This invention relates to reaction products of alumina trihydrate, dimethyl methylphosphonate and a phosphonic acid and the use of such reaction products as flame retardant additives for polymers.

European Patent Publication EP 0245207 describes and claims compositions comprising a halogen-free polymer and, as flame retardant, a metal or metalloid salt of an alkylphosphonic acid or a substituted alkylphosphonic acid such as aluminium methyl methylphosphonate. In EP 0327496 there is described a process for producing metal or metalloid salts of methyl methylphosphonic acid, including the aluminium salt, which comprises reacting, under non-aqueous conditions, dimethyl methylphosphonate with a finely divided form of the oxide or hydroxide of the metal or metalloid, for example trihydrated alumina.

Polymer compositions containing salts as described in the above mentioned publications, and articles such as mouldings made by processing such compositions, generally have good flammability characteristics. It is frequently desired to include titanium dioxide as a pigment in these compositions to give white finished articles. The inclusion of titanium dioxide in amounts conventional for its use as a pigment tend to render the polymer compositions less flame retardant.

It has now been found, surprisingly, that novel products obtained by reacting alumina trihydrate, dimethyl methylphosphonate and a phosphonic acid impart very good flame retardance to polymer compositions, including those containing titanium dioxide.

Accordingly, the present invention provides a reaction product of alumina trihydrate, dimethyl methylphosphonate and a phosphonic acid of formula

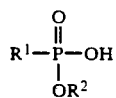

where $R^1$ denotes an alkyl group of 1 to 4 carbon atoms, optionally substituted by at least one group selected from a hydroxyl group, a carboxyl group or a phosphonic acid group $-P(=O)(OH)_2$, or a $C_6$ to $C_{12}$ aryl group and $R^2$ denotes a hydrogen atom or an alkyl group of 1 to 4 carbon atoms.

Where $R^1$ in formula I denotes a hydroxylalkyl group, it is usually an alkyl group substituted by one hydroxyl group such as a hydroxymethyl, 2-hydroxyethyl, 2-hydroxypropyl or 3-hydroxypropyl group. When $R^1$ denotes a carboxyl-substituted alkyl group, it may be, for example, a carboxymethyl, 2-carboxyethyl or 2-carboxypropyl group. $R^1$ may denote an alkyl group substituted by both a hydroxyl group and a carboxyl group, for example a hydroxycarboxymethyl group. Where $R^1$ denotes an alkyl group substituted by a phosphonic acid group, it may be, for example, a 1-hydroxy-1-phosphonoethyl or hydroxyphosphonomethyl group. $R^1$ as $C_6$ to $C_{12}$ aryl is usually aryl hydrocarboxyl for example phenyl, naphthyl, or $C_7$-$C_{12}$ alkylphenyl such as tolyl or xylyl.

Suitable acids of formula I thus include phosphonoacetic acid, alpha-hydroxyphosphonoacetic acid, 2-phosphonopropionic acid, 2-methyl-3-phosphonopropionic acid, 1-hydroxyethylidene-1,1-diphosphonic acid, hydroxymethylene diphosphonic acid, phenylphosphonic acid, naphthylphosphonic acid and mono $C_1$-$C_4$ alkyl derivatives of such acids.

Preferably, $R^1$ denotes a $C_1$-$C_4$ alkyl group which is unsubstituted or substituted by one carboxyl group, by one hydroxyl group and one carboxyl group, or by one hydroxyl group and one phosphonic acid group, or $R^1$ denotes a $C_6$ to $C_8$ aryl group. Especially preferred groups $R^1$ are methyl, carboxymethyl, hydroxycarboxymethyl, 1-hydroxy-1-phosphonoethyl and phenyl groups.

$R^2$ preferably denotes a hydrogen atom or a methyl group. Thus preferred acids include methylphosphonic acid, ethylphosphonic acid, n-propylphosphonic acid, methyl methylphosphonic acid, methyl ethylphosphonic acid, phosphonoacetic acid, methyl phosphonoacetic acid, 2-phosphonopropionic acid, alpha-hydroxyphosphono-acetic acid, hydroxymethylene diphosphonic acid, 1-hydroxyethylidene-1,1-diphosphonic acid, phenylphosphonic acid and tolylphosphonic acids. Especially preferred acids of formula I are methylphosphonic acid, methyl methylphosphonic acid, phosphonoacetic acid, alpha-hydroxyphosphonoacetic acid, 1-hydroxyethylidene-1,1-diphosphonic acid and phenylphosphonic acid.

The flame retardant reaction product of the invention may be obtained by heating alumina trihydrate, dimethyl methylphosphonate and the phosphonic acid of formula I together, usually at a temperature of 100° to 200° C., preferably at 150° to 180° C. The reaction is preferably carried out in a solvent, which may be excess dimethyl methylphosphonate or an inert solvent such as xylene or chlorobenzene, and methanol formed during the reaction is distilled off. In especially preferred embodiments of the invention, the reaction is carried out under reflux using excess dimethyl methylphosphonate as the solvent.

The alumina trihydrate is preferably used in finely divided form, the preferred particle size being 2 microns or less, especially 1 micron or less. The amount of phosphonic acid may be from 5 to 80% by weight, preferably 10 to 50% by weight, based on the weight of the alumina trihydrate. The dimethyl methylphosphonate may be used in a stoichiometric amount for reaction with the alumina trihydrate or, as hereinbefore described, it may be used in excess to act as reaction solvent. In the latter case, the weight ratio of dimethyl methylphosphonate to alumina trihydrate is preferably at least 10:1, especially from 20:1 to 50:1.

The reaction product of the invention is useful as a flame retardant additive in polymer compositions. Accordingly, the invention also provides a composition comprising (A) a polymer and (B) as flame retardant additive, an effective amount of a reaction product of the invention as hereinbefore described.

In polymer compositions of the invention, the additive (B) may be present in an amount of 1 to 100%, preferably 1 to 40% and especially 5 to 15%, by weight based on the weight of the polymer (A). The optimum amount used generally depends on the nature of the polymer and may be determined by simple experiment. The additive (B) may be used in various physical forms depending on the nature of the polymer (A) and the desired properties. For instance, the salt may be ground to a finely divided form to enable better dispersion throughout the polymer.

In accordance with the present invention, polymer compositions having a very good flame retardance can be obtained even when titanium dioxide is included in such compositions as a pigment. When included, the titanium dioxide is usually present in an amount of 0.1 to 30%, preferably 0.5% to 15%, by weight based on the weight of the polymer (A). Particles of the dioxide may have a coating of a white hydrous oxide such as silica or alumina, as in many commercial variants of titanium dioxide supplied for use in polymer compositions, to improve the dispersibility of the dioxide in the polymer. The particles may have a coating of an organic material; dimethylsiloxane, pentaerythritol and triethanolamine have been widely used to coat titanium dioxide for use in polymer compositions.

Examples of polymers (A) which may be flame retardant are:

1. Polyphenylene oxides and sulfides, and blends of these polymers with styrene graft polymers or styrene copolymers such as high impact polystyrene, EPDM copolymers with rubbers, as well as blends of polyphenylene oxide with polyamides and polyesters.
2. Polyurethanes which are derived from polyethers, polyesters or polybutadienes with terminal hydroxyl groups on the one side and aliphatic, cycloaliphatic or aromatic polyisocyanates on the other side including polyisocyanurates, as well as precursors thereof.
3. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenyleneisophthalamide, as well as copolymers thereof with polyethers, such as polyethylene glycols, polypropylene glycols or polytetramethylene glycols.
4. Polyesters which are derived from dicarboxylic acids and dihydric alcohols and/or from hydroxycarboxylic acids or the corresponding lactones, such as polyethylene terephthalate, polybutylene terephthalate, poly-1,4-dimethylol-cyclohexane terephthalate and polyhydroxybenzoates as well as block-copoly-ether-esters derived from polyethers having hydroxyl end groups.
5. Unsaturated polyester resins which are derived from copolyesters of saturated and unsaturated dicarboxylic acids with polyhydric alcohols, together with vinyl compounds as cross-linking agents.
6. Polystyrene.
7. Graft copolymers of styrene, such as, for example, styrene on polybutadiene, styrene and acrylonitrile on polybutadiene, styrene and alkyl acrylates or methacrylates on polybutadiene, styrene and acrylonitrile on polyacrylates or polymethacrylates, styrene and acrylonitrile on acrylate/butadiene copolymers, as well as mixtures thereof with random copolymers of styrene or alpha-methylstyrene with dienes or acrylic derivatives, for instance the polymer mixtures known as ABS, MBS, ASA or AES polymers.
8. Epoxide resins such as polyglycidyl ethers of polyhydric alcohols or phenols, preferably of bisphenols, particularly bisphenol A diglycidyl ethers, or cycloaliphatic diepoxides, together with curing agents therefore.
9. Polycarbonates, including homopolycarbonates and copolycarbonates of bisphenols, especially those based on bisphenol A.
10. Blends of styrene polymers 7 as hereinbefore defined, especially ABS polymers, with polycarbonates 9 as hereinbefore described.

Especially useful compositions of the invention include those where the polymer (A) is a polyphenylene oxide, a polyphenylene sulphide or a blend of said oxide or sulphide with a copolymer and/or graft polymer of styrene, particularly a blend of polyphenylene oxide with high impact polystyrene.

The compositions of the invention may also contain other conventional ingredients, such as heat stabilisers, light stabilisers, ultra-violet light absorbers, antioxidants, antistatic agents, preservatives, adhesion promoters, fillers, pigments, lubricants, blowing agents, fungicides, plasticisers, processing aids, other fire-retardant additives and smoke suppressants.

Other fire retardant additives which may be used together with the additive (B) include phosphorus-containing esters and salts, for example triaryl phosphates such as triphenyl phosphate and alkylated derivatives thereof, e.g. isopropylated derivatives thereof as described in U.S. Pat. No. 3,576,923, resorcinol tetraphenyl bisphosphate, alkyl aryl phosphates such as 2-ethylhexyl diphenyl phosphate and isodecyl diphenyl phosphate, and ammonium polyphosphate; halogen-containing, especially bromine and chlorine-containing, compounds such as decabromodiphenyl ether, hexachlorocyclopendadiene, brominated polystyrene, bromoalkyl-substituted aromatic compounds, haloalkyl phosphates and haloalkyl phosphonates; and metal compounds such as antimony oxide, hydrated alumina, bismuth oxide, molybdenum oxide and mixtures of these compounds with zinc and/or magnesium oxides or salts.

The invention is illustrated by the following Examples, in which parts and percentages are by weight unless stated otherwise.

EXAMPLE 1

Dimethyl methylphosphonate (1300 parts), trihydrated alumina having an average particle size of 1 micron (26 parts) and methylphosphonic acid (13 parts) are heated under reflux, with stirring, for 8 hours. Volatile material evolved during this period, amounting to 26 parts, is collected. The precipitate formed in the reaction mixture is filtered off, washed twice with 250 ml of methanol and subsequently dried at 120° C. under vacuum to constant weight, to give 110.8 parts of a solid product which does not melt at temperatures up to 250° C.

EXAMPLE 2

The procedure for Example 1 is repeated, but using 650 parts of dimethyl methylphosphonate and 6.5 parts of methylphosphonic acid instead of the amounts used in Example 1. Distillate collected during the heating amounted to 15 parts. 114.1 parts of a product which is solid up to 250° C. is obtained.

EXAMPLE 3

The procedure of Example 1 is repeated, but replacing the methylphosphonic acid by methyl methylphosphonic acid (2.6 parts), to give 27.6 parts of distillate and 111.5 parts of solid product which does not melt at temperatures up to 250° C.

EXAMPLE 4

The procedure of Example 3 is repeated, but increasing the amount of methyl methylphosphonic acid to 6.5 parts, to give 19.0 parts of distillate and 109.5 parts of solid product which does not melt at temperatures up to 250° C.

EXAMPLE 5

Dimethyl methylphosphonate (650 parts), trihydrated alumina having an average particle size of 1 micron (26 parts) and phosphonoacetic acid (13 parts) are heated under reflux, with stirring for 8 hours. Volatile material evolved during this period, amounting to 33 parts, is collected. The precipitate formed in the reaction mixture is filtered off, washed twice with 250 ml methanol and subsequently dried at 120° C. under vacuum to constant weight to give 109.5 parts of a white solid product which does not melt at temperatures up to 250° C.

EXAMPLE 6

The procedure of Example 5 is repeated but using 13 parts of phenylphosphonic acid instead of phosphonoacetic acid. Distillate collected during the heating amounts to 27 parts. 108.6 Parts of solid product, which does not melt at temperatures up to 250° C., are obtained.

EXAMPLE 7

The procedure of Example 5 is repeated but using 13 parts of alpha-hydroxyphosphonoacetic acid instead of phosphonoacetic acid. Distillate collected amounts to 53 parts. 100.7 parts of solid product, which does not melt at temperatures up to 250° C., are obtained.

EXAMPLE 8

The procedure of Example 5 is repeated but using 13 parts of 1-hydroxyethylidene-1,1-diphosphonic acid instead of phosphonoacetic acid. Distillate collected amounts to 24 parts. 107 parts of solid product, which does not melt at temperatures up to 250° C., are obtained.

EXAMPLES 9-12

Polymer compositions are prepared from a mixture of a blend of polyphenylene oxide (35 parts) and high impact polystyrene (65 parts) and, as flame retardant additive, one of the solid products of Examples 1 to 4 (10 parts). The mixture is melt-extruded at 270° C. using a twin screw compounding extruder. The resulting extrudate is pelletised and injection moulded to give test bars of 1.6 mm thickness which are subjected to the Underwriters Laboratories Subject 94 (UL 94) test procedure for assessing flammability performance.

The results obtained for the compositions containing different flame retardant additives are given in Table 1. UL 94 classifications of 94 V-0, 94 V-1 and 94 V-2 indicate decreasing level of flame retardant performance under the test conditions, while classification FB indicates that the composition "freely burns", i.e. fails to meet the requirements of 94 V-2.

TABLE 1

| Example No. | Additive | UL 94 Class |
| --- | --- | --- |
| 9 | Example 1 | 94 V-O |
| 10 | Example 2 | 94 V-1 |
| 11 | Example 3 | 94 V-1 |
| 12 | Example 4 | 94 V-1 |

EXAMPLE 13

The procedure of Examples 9 to 12 is repeated for a composition as used in Example 9 but also including 7.5 parts of ®Kronos CL 220, a titanium dioxide available from NL Chemicals Limited. The test result classifies this composition as 94 V-1, indicating that the inclusion of titanium dioxide does not prevent the composition from achieving a very good level of flame retardance in this test.

EXAMPLES 14-17

The procedure of Examples 9 to 12 is repeated for compositions as used in those Examples, but containing one of the products of Examples 5 to 8 (10 parts) instead of the product of Examples 1 to 4 and also including 5 parts of ®Kronos CL 220. The results obtained are given in Table 2.

TABLE 2

| Example No. | Additive | UL 94 Class |
| --- | --- | --- |
| 14 | Example 5 | 94 V-1 |
| 15 | Example 6 | 94 V-1 |
| 16 | Example 7 | 94 V-1 |
| 17 | Example 8 | 94 V-1 |

These results show that inclusion of titanium dioxide does not prevent polymer compositions from achieving a very good level of flame retardance.

What is claimed is:

1. A reaction product of alumina trihydrate, dimethyl methylphosphonate and a phosphonic acid of formula I

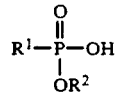

where $R^1$ denotes an alkyl group of 1 to 4 carbon atoms, or an alkyl group of 1 to 4 carbon atoms substituted by at least one group selected from a hydroxyl group, a carboxyl group or a phosphonic acid group —P(=O)-(OH)$_2$, or a $C_6$ to $C_{12}$ aryl group and $R^2$ denotes a hydrogen atom or an alkyl group of 1 to 4 carbon atoms, the amount of phosphonic acid being within the range of from 5 to 80% by weight of the alumina trihydrate, and dimethyl methylphosphonate being in a stoichiometric amount for reaction with the alumina trihydrate or being in excess of said stoichiometric amount.

2. A product according to claim 1, in which $R^1$ denotes a $C_1$ to $C_4$ alkyl group which is unsubstituted or substituted by one carboxyl group, by one hydroxyl group and one carboxyl group, or by one hydroxyl group and one phosphonic acid group, or $R^1$ denotes a $C_6$ to $C_8$ aryl group.

3. A product according to claim 2, in which $R^1$ denotes a methyl, carboxymethyl, hydroxycarboxymethyl, 1-hydroxy-1-phosphonoethyl or phenyl group.

4. A product according to claim 1, in which $R^2$ denotes a hydrogen atom or a methyl group.

5. A product according to claim 1, in which the acid of Formula I is methylphosphonic acid, methyl methylphosphonic acid, phosphonoacetic acid, alpha-hydroxyphosphonoacetic acid, 1-hydroxyethylidene-1,1-diphosphonic acid or phenylphosphonic acid.

6. A process for the preparation of a product according to claim 1, which comprises heating alumina trihydrate, dimethyl methylphosphonate and the phosphonic acid together at a reaction temperature of 100° to 200° C.

7. A process according to claim 6, in which the reaction temperature is 150° to 180° C.

8. A process according to claim 6, in which the reaction is carried out in a solvent.

9. A process according to claim 8, in which the reaction is carried out under reflux using excess dimethyl methylphosphonate as the solvent.

10. A process according to claim 6, in which the amount of the phosphonic acid is from 10 to 50% by weight of the alumina trihydrate.

11. A process according to claim 6, in which the alumina trihydrate has a particle size of 2 microns or less.

12. A composition comprising (A) a polymer and (B) as flame retardant additive, an effective amount of a product according to claim 1.

13. A composition according to claim 12, in which the acid of Formula I is methylphosphonic acid, methyl methylphosphonic acid, phosphonoacetic acid, alpha-hydroxyphosphonoacetic acid, 1-hydroxyethylidene-1,1-diphosphonic acid or phenylphosphonic acid.

14. A composition according to claim 12, in which the amount of (B) is from 1 to 40% by weight, based on the weight of the polymer (A).

15. A composition according to claim 12, in which the amount of (B) is from 5 to 15% by weight, based on the weight of the polymer (A).

16. A composition according to claim 12, which also contains 0.1 to 30% by weight, based on the weight of the polymer (A), of titanium dioxide.

17. A composition according to claim 16, which contains 0.5 to 15% by weight, based on the weight of the polymer (A), of titanium dioxide.

18. A composition according to claim 12, in which the polymer (A) is a polyphenylene oxide, a polyphenylene sulphide or a blend of said oxide or sulphide with a copolymer or graft polymer of styrene.

19. A composition according to claim 18, in which the polymer (A) is a blend of polyphenylene oxide with high impact polystyrene.

20. A product according to claim 1 wherein the weight ratio of dimethyl methylphosphonate to alumina trihydrate is from 10:1 to 50:1.

* * * * *